United States Patent [19]
Ryden

[11] Patent Number: 5,452,480
[45] Date of Patent: Sep. 26, 1995

[54] SKI GOGGLES

[75] Inventor: William D. Ryden, Colorado Springs, Colo.

[73] Assignee: Electric Eyewear Systems, Inc., Colorado Springs, Colo.

[21] Appl. No.: 227,451

[22] Filed: Apr. 15, 1994

[51] Int. Cl.⁶ ........................................... A61F 9/02
[52] U.S. Cl. .................................. 2/436; 2/171.3
[58] Field of Search ................ 2/436, 437, 171.3, 2/8, 9

[56] References Cited

U.S. PATENT DOCUMENTS

| | | |
|---|---|---|
| 2,526,737 | 10/1950 | Farina . |
| 2,539,284 | 1/1951 | Thomas . |
| 3,015,987 | 1/1962 | Harrison . |
| 3,377,626 | 4/1968 | Smith . |
| 3,691,565 | 9/1972 | Galonek ............................. 2/436 X |
| 3,825,953 | 7/1974 | Hunter . |
| 4,150,443 | 4/1979 | McNeilly . |
| 4,238,857 | 12/1980 | Waters ................................. 2/171.3 |
| 4,443,893 | 4/1984 | Yamamoto ...................... 2/171.3 X |
| 4,575,875 | 3/1986 | Dawson et al. . |
| 4,951,662 | 4/1990 | Townsend, Jr. . |

*Primary Examiner*—Peter Nerbun
*Attorney, Agent, or Firm*—Linda Flewellen Gould

[57] ABSTRACT

Goggles and eyeglasses worn in winter weather conditions are subject to fogging. A method of preventing condensation from forming on goggles and on eyeglasses worn under goggles is provided. The method involves using a fan to exhaust air from the air space between the goggles and a user's face. Continuous operation of the fan is designed to be inaudible and effective to prevent fogging. The method can involve use of a goggle ventilation design which improves wearer comfort. The goggle can also clear fogging which has occurred while the fan is not in operation.

11 Claims, 7 Drawing Sheets

SKI GOGGLES

1.0 BACKGROUND OF THE INVENTION

1.1. Technical Field

This invention relates to an improved ski goggle which is comfortable to wear, prevents goggle lens fogging, prevents lens fogging of eyeglasses worn under the goggle, and avoids audible noises from a fan used to prevent lens fogging.

1.2. Background Art

Modern ski goggles attempt to achieve a number of design goals dictated by operation in a harsh winter environment. These design goals include attenuation of bright outside visible light, elimination of ultraviolet solar radiation, maximizing visual recognition of snow pack features in both high and low light levels, prevention of goggle lens fogging, prevention of fogging of eyeglasses worn under a goggle, and exclusion of various other outside harsh weather environments. These goals need to be achieved via means which do not generally impede motion of a skier, which do not detract from positive aspects of the skiing environment, and which can be offered commercially at reasonable prices.

Modern ski goggles, as are widely available commercially and as are further described in the prior art (see U.S. Pat. Nos. 3,377,626 to Smith and 4,150,443 to McNeilly) employ a design compromise characterized by over ventilation when a skier is in motion and under ventilation when the skier is at rest. This over ventilation results in uncomfortable wind chill effects on the skier's face and eyes, rapid temperature decrease of goggle and eyeglass lenses, and lens fogging when the skier's exhaled breath enters the goggle air space. When the skier comes to rest after vigorous skiing activity, under ventilation causes the dew point of the goggle air space to rise rapidly via expiration of water vapor from the skier's eyes, and intake of skier's exhaled breath. This elevated dew point, if it exceeds the decreased lens temperature, results in lens fogging.

A number of techniques are known in the art which minimize or eliminate such ski eyewear fogging. U.S. Pat. No. 2,526,737 to Farina discloses the use of a breath powered exhaust fan; Smith discloses an insulated goggle lens; McNeilly and U.S. Pat. No. 3,825,953 to Hunter disclose the use of an electric fan; U.S. Pat. No. 4,868,929 to Curcio discloses an electrically heated goggle lens; U.S. Ser. No. 07/947,740, filed by Ryden, the applicant herein, discloses electrically heated eyeglasses.

Farina discloses use of exhaust fans to remove moist air from the goggle space in front of the eyes. The shaft of this fan is shared with a turbine which is made to rotate by constraining the exhaled skier's breath to flow through the turbine and thereby rotate the fan shaft. This fan means is quite inconvenient to use on a continuous basis and is also impractical for operation at predetermined fan speeds. Furthermore, Farina does not address the use of eyeglasses under a goggle.

Smith discloses a multi-component lens goggle to increase the temperature of the innermost lens. This practice reduces goggle lens fogging, but is ineffective in preventing fogging of an eyeglass worn under a goggle. Smith also discloses an improved ski goggle that uses an air permeable goggle frame, so that the goggle air space is in slow but controlled air exchange with the outside air, thereby keeping the air inside the goggle and the skier's face warm but also preventing moisture accumulation. It is readily understood that such an air permeable frame may be advantageous over an open frame, such as that of an eyeglass; and advantageous over a closed frame that would allow moisture accumulation. Such an air permeable frame shows significant goggle air space temperature variation depending on the rate of skier motion. Use of an eyeglass under such a goggle will result in eyeglass lens fogging due to this temperature variation and intake of exhaled skier breath through the air permeable frame.

McNeilly and Hunter are both effective at preventing goggle fogging and McNeilly specifically discloses features intended to defog an eyeglass worn under a goggle. McNeilly relies on open goggle ventilation as disclosed by Smith for effective defogging of the McNeilly goggle. Consequently, McNeilly suffers from the over ventilation problem discussed above. Additionally, the electric fans used in both McNeilly and Hunter produce sound levels which are very annoying to the skier and, consequently, in practice, the fans are only operated to defog lenses as opposed to preventing fogging from occurring. This annoying sound level (estimated at 35 decibels) is due to the high fan blade rotational speed required to produce the desired defogging effect when using small fans of the type appropriate for mounting on or near a goggle.

Three examples of the usage of fans in ski goggles are commercially available. One of these is manufactured by Smith Sport Optics, Inc., assignee of the McNeilly patent. The other two examples are sold under the trademarks Uvex (Germany) and Swans (Japan) respectively. All of these commercial goggles exhibit the annoying sound level of McNeilly.

Electrical heating of goggles as practiced by Curcio or electrical heating of eyeglasses as practiced by Ryden are effective in preventing fogging. Ryden is silent in operation, and provides fog-free vision for eyeglasses with or without the use of goggles. A disadvantage of Ryden is that effective lens heating under a goggle requires about one watt of electrical power, and this level of power consumption for a full day of winter sports activity necessitates the use of a battery pack which is not comfortably mountable on the eyeglass or goggle.

While the methods disclosed in the prior art are effective in reducing or preventing fogging of winter sports eyewear, each has one or more deficiencies which detract from fully satisfactory use to achieve their intended defogging function. Accordingly, there is a need for an improved ski goggle which prevents goggle lens fogging and eyeglass lens fogging when worn under the improved goggle. Operation of the defogging means should be undetectable by the skier and self-contained on the goggle. Additionally, an improved ski goggle needs to provide a uniform level of comfort to the skier's face and eyes, irrespective of whether the skier is in rapid motion.

2.0 DISCLOSURE OF THE INVENTION

2.1 SUMMARY OF THE INVENTION

An object of this invention is to provide a generally improved ski goggle which can be used in winter sports without fogging the lenses of the goggle or the lenses of eyeglasses worn under the goggle.

Another object of this invention is to provide such an improved goggle which continuously uses an electric fan to prevent fogging, without creating distracting noise.

Yet another object of this invention is to provide such an improved goggle with a fog prevention mechanism which is self-contained on the goggle and operable for at least a full day of winter sports activity without intervention by the goggle wearer.

A still further object of this invention is to provide a uniform level of comfort to a skier's face and eyes, irrespective of whether the skier is in rapid motion, while the goggle is worn. The improved ski goggle disclosed here relies on a new method of electric fan operation to prevent goggle fogging. This new fan operation method allows for continuous and silent fan operation. Use of the fan, as disclosed here, also advantageously allows use of a much restricted goggle ventilation design, thereby resulting in higher goggle air space temperatures and reduced wind chill effects when the skier is in motion. This new fan operation method consumes 1/10 to 1/100 the electrical power of heated eyeglasses, and thereby allows needed batteries to be self-contained on a goggle.

The operation of this method of preventing lens fogging is generally understood from an examination of the causes of goggle lens fogging and of eyeglass lens fogging when such eyeglass is worn under a goggle (referred to herein as a "related eyeglass"), and detailed measurements presented herein. Any surface will accumulate water vapor when the temperature of the surface is lower than the dew point temperature of the adjacent air. In a ski goggle environment, lens temperature and dew point are both subject to frequent change which may result in lens fogging. Two sources of water vapor increase the goggle air space dew point temperature (the "Dew Point") above that generally prevailing in the skier's absence: the skier's face, including the eyes, tears therefrom, and skin; and the exhaled breath of the skier. Ventilation of the goggle air space by rapid skier motion causes lens temperatures to fall.

Exhaled breath readily enters the air space within a modern goggle due to the air pervious nature of the goggle frame. Although this may seem obvious, neither Smith nor McNeilly suggest this as a major source of goggle or related eyeglass fogging. When the skier is in motion, the air stream around the skiers head tends to force exhaled breath into the goggle and results in intermittent lens fogging. Additionally, in very cold weather the skier is likely to wear protective garments about the nose and mouth, which channel the skier's exhaled breath into the goggle. It is apparent that making the goggle frame generally impervious to air flow would eliminate this water vapor source. However, such an air impervious frame alone, would substantially worsen lens fogging from the water vapor sources inside the goggle.

The invention disclosed herein eliminates water vapor produced inside the goggle air space by using a new goggle ventilation technique which is understood based on data reported here and obtained using an electronic instrument (Fisher Scientific digital hygrometer/thermometer, catalog number 11-661-7B) which measures air temperature, and air water vapor content (given as dew point and relative humidity). The water vapor sensor of this instrument is capable of fast response time (2 seconds) and is small enough that it can be placed in the air space between the eye and an eyeglass. The temperature and water vapor content measurements of this instrument have a calibration traceable to the National Institute of Standards and Tests.

Goggle and eyeglass lens temperatures have been measured for tests reported herein using a digital thermometer with two thermocouple probes (Simpson, Model 383).

Table 1 summarizes test results conducted during the design of the improved goggle claimed herein. Table 1 gives the time in seconds for the relative humidity within a small fan ventilated inclosure to change from a value of 100% to 60%. This inclosure has an air volume roughly equivalent to that of a ski goggle and has various access ports to accommodate introduction of water vapor, mounting of ventilation fans, outside air access, and insertion of various measurement probes. The data of Table 1 was obtained with a water vapor source (water) having an exposed circular area of 2.5 centimeters diameter and 130° F. temperature. Data for two types of fan ventilation configurations are shown, one being in accordance with McNeilly and the other being direct air exhaust. The data is shown as a function of fan volumetric capacity, measured in cubic feet per minute (CFM). The data of Table 1 suggests that direct air exhaust is more effective at fog prevention and removal than the air circulation technique of McNeilly. This is confirmed using a test described below in which an operative example of McNeilly and a modified version of McNeilly are compared.

TABLE 1

Time (in seconds) required
for fan ventilation to decrease
the relative humidity of a small inclosure
from 100% to 60%.

| VENTILATION TYPE | FAN CAPACITY (CFM) | TIME (SECONDS) |
|---|---|---|
| Direct Exhaust | 1.3 | 3.0 |
| | 0.97 | 5.5 |
| | 0.74 | 6.8 |
| | 0.49 | 8.0 |
| | 0.18 | 42.0 |
| Air Circulation | 2.1 | 110.0 |

Another test procedure employed in developing the invention claimed herein is to observe fogging of related eyeglasses using various goggle embodiments under closely controlled conditions. In this test procedure the related eyeglass is slowly cooled in a refrigerated chamber to 12° F. above the ambient dew point. The cooled eyeglass is then positioned normally over the eyes, and the experimental goggle embodiment is placed over the related eyeglass. This latter procedure is carried out at about 70° .F, with ambient dew point at 30° F. ±5° F. Fogging of the related eyeglass lenses is then observed, either to determine the ability of the experimental goggle embodiment to prevent related eyeglass fogging or, if the related eyeglass is allowed to fog, to determine the ability of the experimental goggle to clear fogging. Evaluation of a typical, modern ski goggle using this technique will result in related eyeglass fogging within one minute with such fogging persisting for over five minutes. This technique has been found to be a reliable indicator of the ability of a given goggle to prevent or clear related eyeglass fogging in a broad range of actual skiing conditions. Use of this technique indicates that prior art practice is ineffective with regard to achieving the specified goals of the present invention. This test procedure is referred to below as the "Fogging Test".

An operative embodiment of McNeilly is available commercially from Smith Sport Optics, Inc., and is referred to herein as the "Smith Fan Goggle". The fan of this goggle has an annoying sound level, estimated at 35 decibels (db), which is largely attributable to sound produced by fan blade rotation of 17,000 RPM. This sound level could be reduced significantly by use of lower fan RPM, but such reduction results in a reduction of fan volumetric capacity. As a result, the Smith Fan Goggle becomes ineffective at either preventing lens fogging or defogging lenses. This is illustrated in the data of Table 2, where results of the Fogging Test (described in the paragraph above) for the Smith Fan Goggle are presented. The time (in seconds) to clear both related eyeglass lenses, and whether fan operation prevented fogging are indicated.

TABLE 2

Results of the Fogging Test on Different Goggles

| Ventilation Type | Fan Capacity (CFM) | Time to Clear (Seconds) | Prevents Fogging |
|---|---|---|---|
| Smith Fan Goggle | 2.1 | 70 | yes |
|  | 0.93 | 180 | no |
|  | 0.62 | no clearing | no |
| Direct Exhaust | 2.1 | 30 | yes |
|  | 0.93 | 35 | yes |
|  | 0.49 | 270 | no |

The defogging performance of the Smith Fan Goggle at 0.93 CFM is marginal and becomes ineffective at 0.62 CFM. As discussed below, the motor type used in the Smith Fan Goggle is loud at any motor speed, but use of appropriate fan motors will not produce quiet operation at the fan capacities required for McNeilly to be effective. As direct exhaust has proven more effective than circulation for dehumidifying, I reversed the direction of rotation of the motor of the Smith Fan Goggle and provided direct access of the fan exhaust to outside of the goggle. This direct exhaust gives superior performance to that of the Smith Fan Goggle as seen by comparing the defogging results for these two goggles given in Table 2. However, it is seen from the results of Table 2 that this method of defogging becomes ineffective at fan capacities below 0.5 CFM.

The Uvex and Swan commercial fan goggles also exhibit annoying sound levels similar to the Smith Fan Goggle. The former goggles, however, operate in the direct exhaust mode. The Swan goggle has the additional feature that the fan can be turned on or off by a mechanism which is controlled by a sensor of relative humidity level within the goggle.

A key feature of the invention disclosed herein is that the ventilation technique disclosed achieves fog-free lenses with reduced fan blade rotational speed, thereby resulting in inaudible fan blade sound emission levels. For example, one embodiment of this invention, using a fan of similar physical size to that used in the Smith Fan Goggle, can operate at 3000 RPM (0.3 CFM) and be inaudible and effective in defogging a related eyeglass. Results of the Fogging Test on this embodiment of the present invention show fog clearing in 45 seconds. Moreover, fogging is prevented while the inaudible fan is in use.

Additional measurements using the digital hygrometer/thermometer indicate that the air temperature within a goggle is elevated by 30° to 40° F. over that of the outside air when the skier is at rest and decreases slowly as a function of the rate of ventilation by outside air. It is also observed that without ventilation the Dew Point is dependent on the temperature within the goggle and will be nearly equal to that temperature. It is also observed that the Dew Point drops rapidly with very low ventilation rates and then slowly approaches the dew point of the outside air. This sudden drop can result in the Dew Point being significantly below the temperature of the air within the goggle and consequently below the temperature of related eyeglass lenses or the goggle lens. This latter condition is most advantageous in preventing fogging of these lens surfaces and the present invention exploits this effect.

The present invention utilizes goggle air replacement rates slightly higher than that needed to effect the above described sudden drop in dew point temperature. Air replacement rates higher or lower than this are less desirable. Higher rates, although effective at fog prevention as indicated by the data of Table 2, lower the goggle internal temperature, making the goggle less comfortable, and produce wind chill effects and sound levels that are annoying to the skier. Lower rates, although generally capable of fog-free performance, may result in occasional fogging which may persist.

Tests of various fan equipped goggles reveal that fan induced air flow within the goggle air space is quite nonuniform. This nonuniform air flow is a major obstacle to effectively defogging related eyeglasses. Such nonuniformity, for example, causes the Dew Point in one region of the goggle to be dependent on the local temperature while the Dew Point in another region is dependent on the outside air dew point. A related eyeglass lens in the former region fogs, while a related eyeglass lens in the latter region remains clear. Proper fan placement and orientation with respect to the goggle frame and related eyeglasses is essential to obtain more uniform air flow within the goggle air space.

A major cause of air flow nonuniformity is the interaction between the circularly symmetric air flow pattern of an isolated fan and the restrictive boundaries of the goggle and related eyeglass. In the case of an exhaust fan placed at the top center of a goggle frame, this interaction results in air flow from one side of the goggle being drawn into the forward side of the fan, while air from the other side of the goggle is drawn into the rear side of the fan. This asymmetric air flow causes the right and left air spaces behind the lenses of a related eyeglass to be exhausted at different rates. This nonuniform air flow can be counteracted by suitable asymmetric placement, modification, or orientation of the fan. Thus in the example above, movement of the fan laterally to one side of the goggle center is effective in equalizing the air flow behind each related eyeglass lens. Another technique which has been found to be effective in this regard is rotation of the fan axis by about 45 degrees about a second axis which passes through the fan from right to left.

Several types of miniature electric motors are capable of driving small fans inaudibly at lower fan RPM. Electric motors of the type used in presently available commercial fan goggles are inexpensive, but generate considerable sound levels from armature winding electrical contacts (brushes), even at low fan RPM. This noise source can be minimized in more expensive versions of this motor type, but not eliminated. Two types of brushless fans are widely available. The first type uses electronic commutators and the second type uses electronic generation of three phase drive voltages and a brushless three phase ac motor.

It is advisable to place a cover over the fan exhaust which has a closed top, but is open on the right and left side. This cover reduces back draft of air into the goggle when the skier is in motion and prevents snow from entering the fan. Snow could melt and refreeze, causing the fan to stall.

A significant advantage of the fan forced ventilation technique used in the present invention is that the size of ventilation ports along the goggle frame can be significantly reduced. Elimination of all ports in the top of the goggle frame except the fan exhaust is particularly advantageous. Small ports in the frame bottom near the cheek bone allow good air flow when related eyeglasses are worn. These ports, however, may allow exhaled breath to enter the goggle and cause brief fogging. When the instant fan forced defogging method is utilized, these bottom ports can also be eliminated. In this case, the two frame ports used to allow passage of eyeglass temple pieces through the goggle frame are relied on as the only air intake ports. The temple ports allow excellent air flow into the goggle along the face where good access is afforded to the space between and eyeglass lens and the eye socket. It has been found that the foam gaskets commonly used in modern goggles to cushion the frame against the face, although air pervious, can effectively block goggle air intake. It is advisable to insure that the temple air intake ports be left unobstructed and in particular not be blocked with this air pervious foam.

It is generally advantageous to minimize the fan power requirements so as to minimize the size and number of batteries required to give suitable fan operation for a reasonable time period. The improved goggle ventilation techniques disclosed herein can advantageously use various electronic means to obtain a high level of power use efficiency. One such electronic technique is pulse width modulation, in which drive voltage is only applied to the motor for a fraction of a repeating duty cycle. In this way variable fan speed is obtainable from a fixed battery voltage with nearly 100% power efficiency.

Another embodiment of the invention described herein advantageously uses electronic fan controls and both temperature sensors and water vapor sensors to effect a predetermined difference between the goggle or related eyeglass lens temperature and the Dew Point. That temperature difference can be minimized in this situation compared to one in which only manual fan controls are used. Placement of the sensors near the fan intake would allow effective sampling of inside air space conditions. The sensors could be mounted on the goggle frame or the fan assembly, or mounted on extensions attached at one end to either the frame or the fan assembly and extending into the area where temperature or water vapor measurement is desired. In the event of a sudden increase of the Dew Point, fan speed could be automatically increased to lower the Dew Point. Such fan operation could significantly lower the power needed to drive the fan while still providing fog-free operation.

2.3 DETAILED DESCRIPTION OF THE PREFERRED EMBODIMENT

Figure 1:
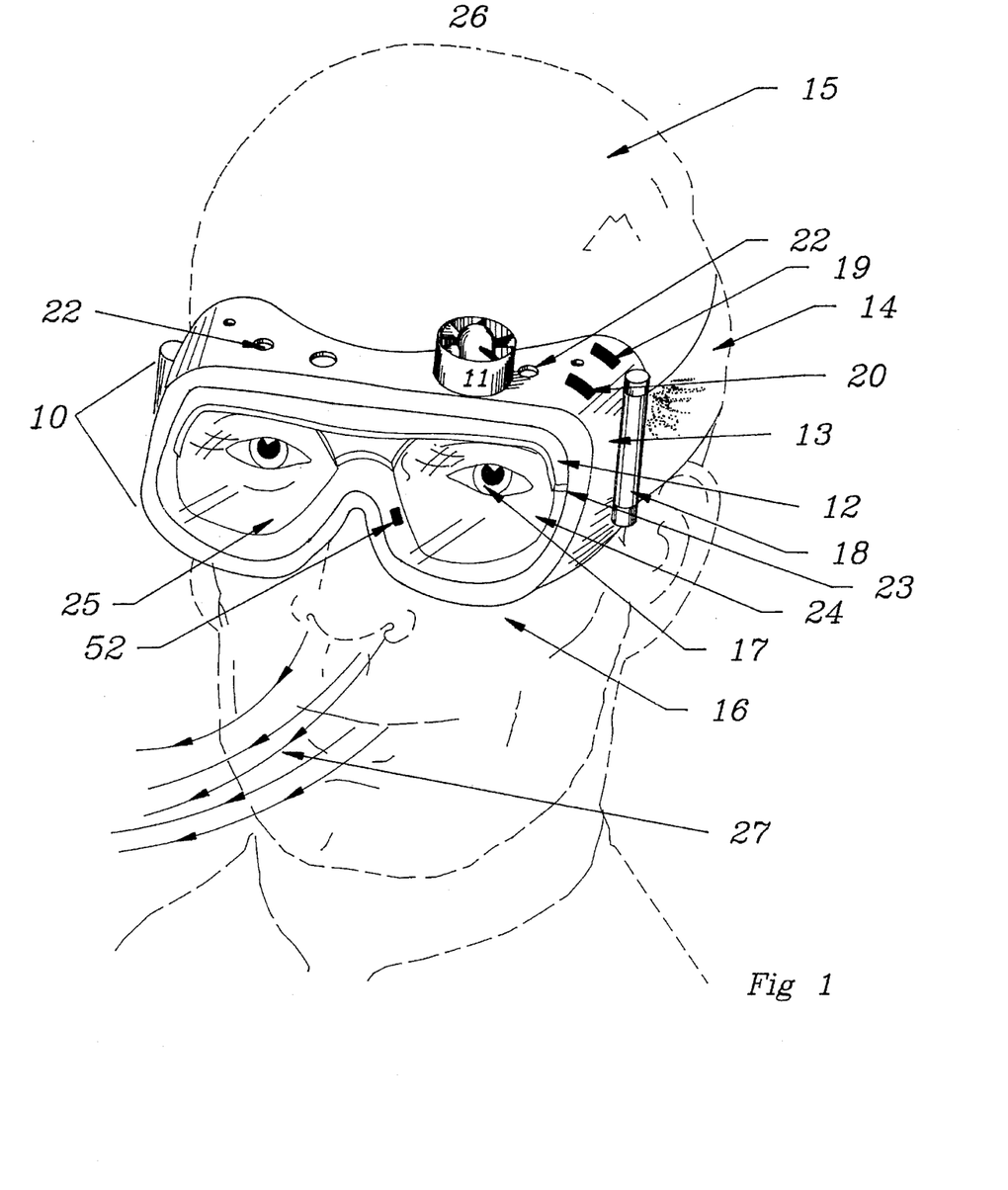
FIG. 1 is a perspective view of a goggle according this invention, depicted on the head of a user.

The general operation and appearance of an improved ski goggle according to the present invention can best be understood by reference to FIG. 1. This improved goggle 10 is comprised of the following structural elements: lens 12, frame 13, and strap 14. Goggle lens 12 is held in place in front of the wearer's eyes 17 by frame 13. The spacing of lens 12 away from face 16 allows related eyeglass 23 to be worn with goggle 10. Frame 13 is comfortably held in place against the wearer's head 15 by use of strap 14, which may advantageously be made of elastic or other flexible material.

Figure 5:
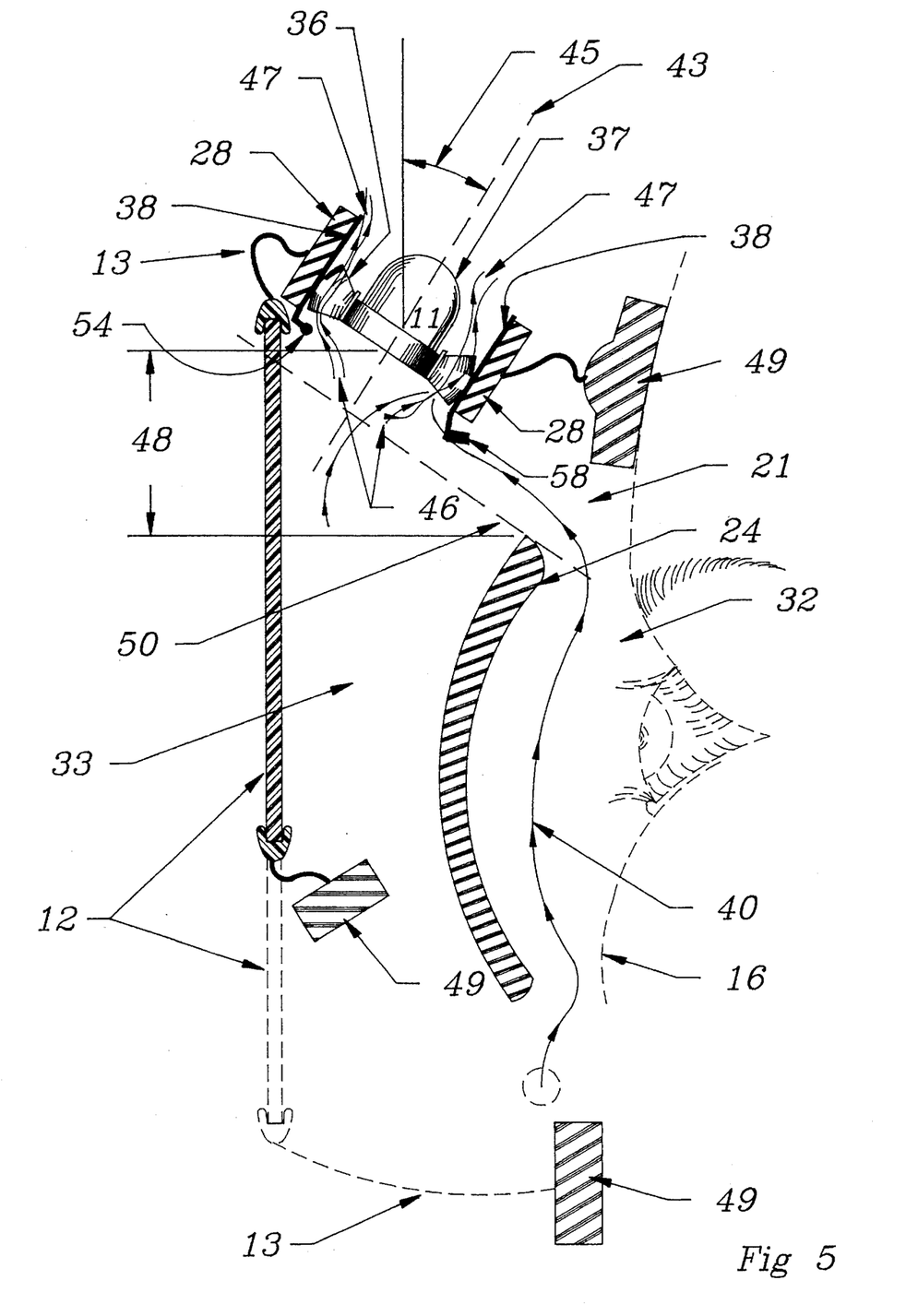
FIG. 5 is a mid-cross sectional view of an embodiment of this invention, taken generally in the plane of line 5—5 of FIG. 3.

The air volume enclosed by lens 12, frame 13, and skier's face 16, forms the goggle air space 21, as shown in FIG. 5. Goggle air space 21 has access to air outside the above boundaries through frame ports 22 and exhaust fan 11. When in operation, fan 11 exhausts air from within the goggle air space 21 directly to the outside of the goggle 10, with exhausted air being replaced by outside air 26 entering the goggle air space 21 through the frame ports 22. It is generally intended that this fan forced ventilation by outside air will reduce the dew point temperature of the goggle air space 21, thereby preventing fogging of the goggle lens 12.

A primary feature of the present invention is the specification of fan operation to minimize fogging of related eyeglass lenses 24,25 while also minimizing fan induced sound and wind chill effects. Two temperatures are found to be important in this regard. The first temperature is the dew point temperature of that portion of goggle air space 21 between lenses 24 or 25 and face 16. This first temperature is referred to herein as dew point T1. The second temperature is the respective temperature of lens 24 or 25. This second temperature is referred to herein as lens temperature T2.

Figure 2:
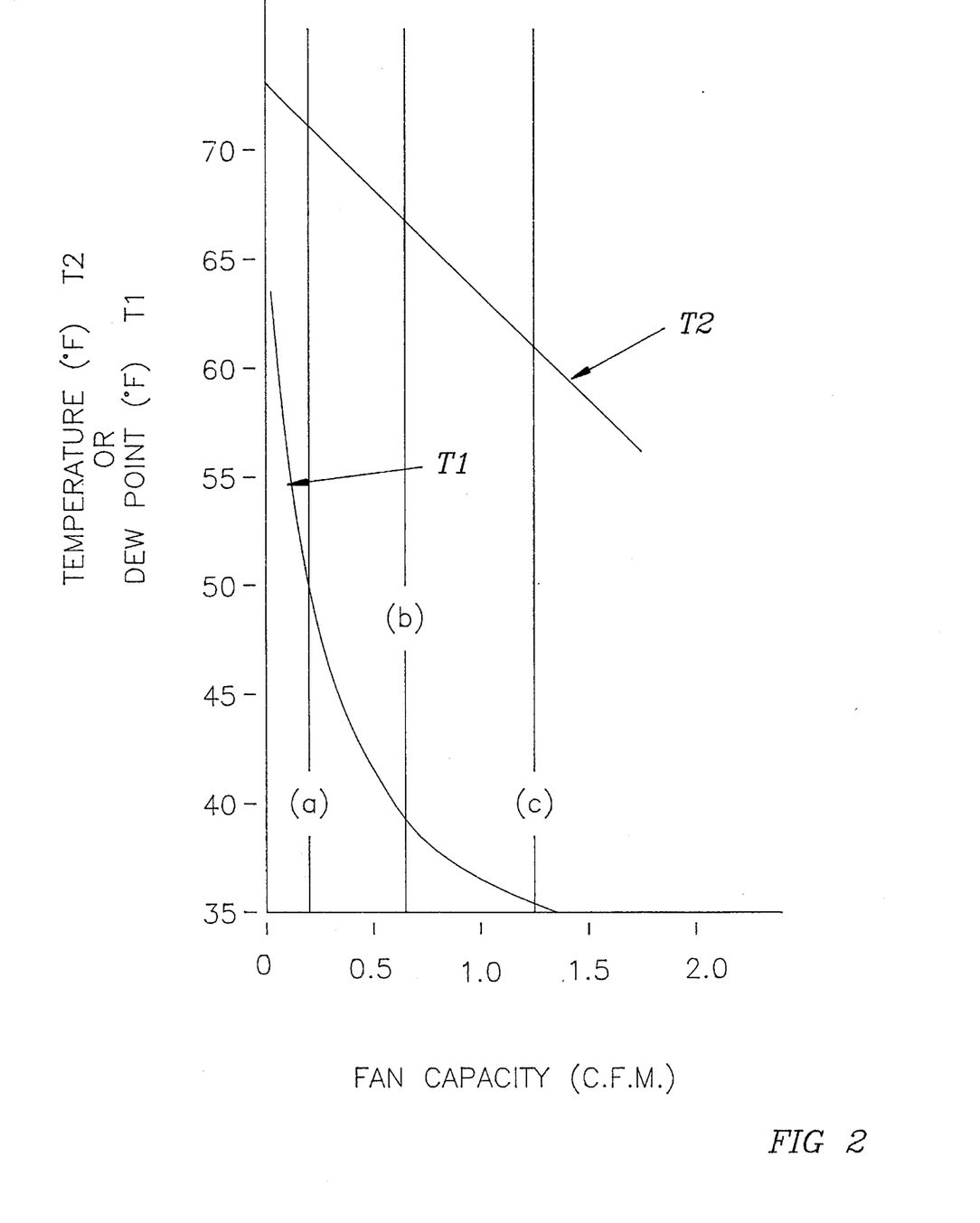
FIG. 2 is a graph of data obtained using an embodiment of this invention in which optimum fan operation range is indicated.

The dependence of dew point T1 and lens temperature T2, in an embodiment of the present invention as illustrated in FIG. 1, is shown in FIG. 2 as a function of fan volumetric capacity measured in cubic feet per minute (CFM). The measurements of dew point T1 were obtained with the digital hygrometer/thermometer referenced in section 2.1. The measurements of lens temperature T2 were obtained with the digital thermocouple thermometer also identified in section 2.1. Measurements of dew point T1 were obtained with the dew point of outside air 26 at 30° F. Measurements of lens temperature T2 were obtained with the temperature of outside air 26 at 25° F. Dew point T1 is seen to fall rapidly at low fan capacity (i.e., less than 0.5 CFM) and then slowly approach the dew point of outside air 26. Lens temperature T2 shows a uniform, but slower decrease.

Eyeglass lenses 24, 25 will fog only if dew point T1 equals or exceeds respective lens temperature T2. In FIG. 2 dew point T1 is not shown to exceed lens temperature T2. However, in an event causing lens fogging, such as vigorous physical exercise or entry of exhaled breath 27 into goggle air space 21, dew point T1 would rise to the temperature (not shown) of the air space between the face 16 and related eyeglass lens 24,25. This temperature is usually above lens temperature T2. Therefore, lens 24 or 25 may fog if adequate water vapor were present in goggle space 21 to cause the necessary rise in dew point T1.

The effect of ventilation at low fan capacity in preventing lenses 24,25 from fogging can be understood from the above discussion and FIG. 2. Ventilation at low fan capacity is seen to result in a significant drop in dew point T1 to a point well below lens temperature T2. This large difference between lens temperature T2 and dew point T1 allows related eyeglass lens 24,25 to remain clear during events which would otherwise have caused lenses 24,25 to fog without fan operation. The effects of operation of fan 11 at various volumetric capacities is further described below.

Operation of fan 11 at capacities less than point (a) of FIG. 2 does not result in large enough reductions in dew point T1 for achieving satisfactory fog prevention. In addition such fan operation is not capable of clearing fog in the event that lens 24 or 25 would fog. Operation of fan 11 at capacities beyond point (b) in FIG. 2 results in smaller differences between lens temperature T2 and dew point T1 than for operation at point (b). Nevertheless, such operation is effective to defog due to the higher air flow rates, but may produce annoying sound levels and wind chill effects. Operation of fan 11 beyond point (c) is not advantageous because both annoying fan sound levels and wind chill effects will occur. Operation of fan 11 between point (a) and point (b) of FIG. 2 is optimum, as good fog prevention is obtained, sound levels are quite low, wind chill effects are low, and any fogging of lenses 24,25 will clear quickly.

A fan 11 may be equipped with a motor control means (not shown) for controlling the fan motor to drive the fan at one of multiple possible speeds. In this embodiment, the motor control means can be utilized to automatically set the fan to the lowest possible speed which will accomplish defogging. In this manner, a speed which is most advantageous from the standpoint of reduced noise and reduced power usage can be automatically chosen as conditions effecting fogging change. To automate this selection of an appropriate fan speed, certain information must be determined on a continuing basis. A lens temperature sensor may be used to continually determine the temperature of the goggle lens 12. Similarly, an air temperature sensor 54, as shown in FIG. 5, may be used to determine the temperature of air adjacent to eyeglass lenses 24, 25. The temperature of the lens 24, 25 is approximately the same as the temperature of the air in the air space 33. A water vapor sensor 58 may be attached to some portion of the frame 13 to detect the level of water vapor presence in the air space 33. The measured water vapor is indicative of the dew point temperature of air within the air space 33. Therefore, once the temperature of the lens 12 or the eyeglass lenses 24, 25 and the water vapor content of the air space 33 are determined, the appropriate fan speed can be calculated and automatically selected by the motor speed controller, to obtain the conditions needed to resist fogging, as shown in FIG. 2.

Figure 4:
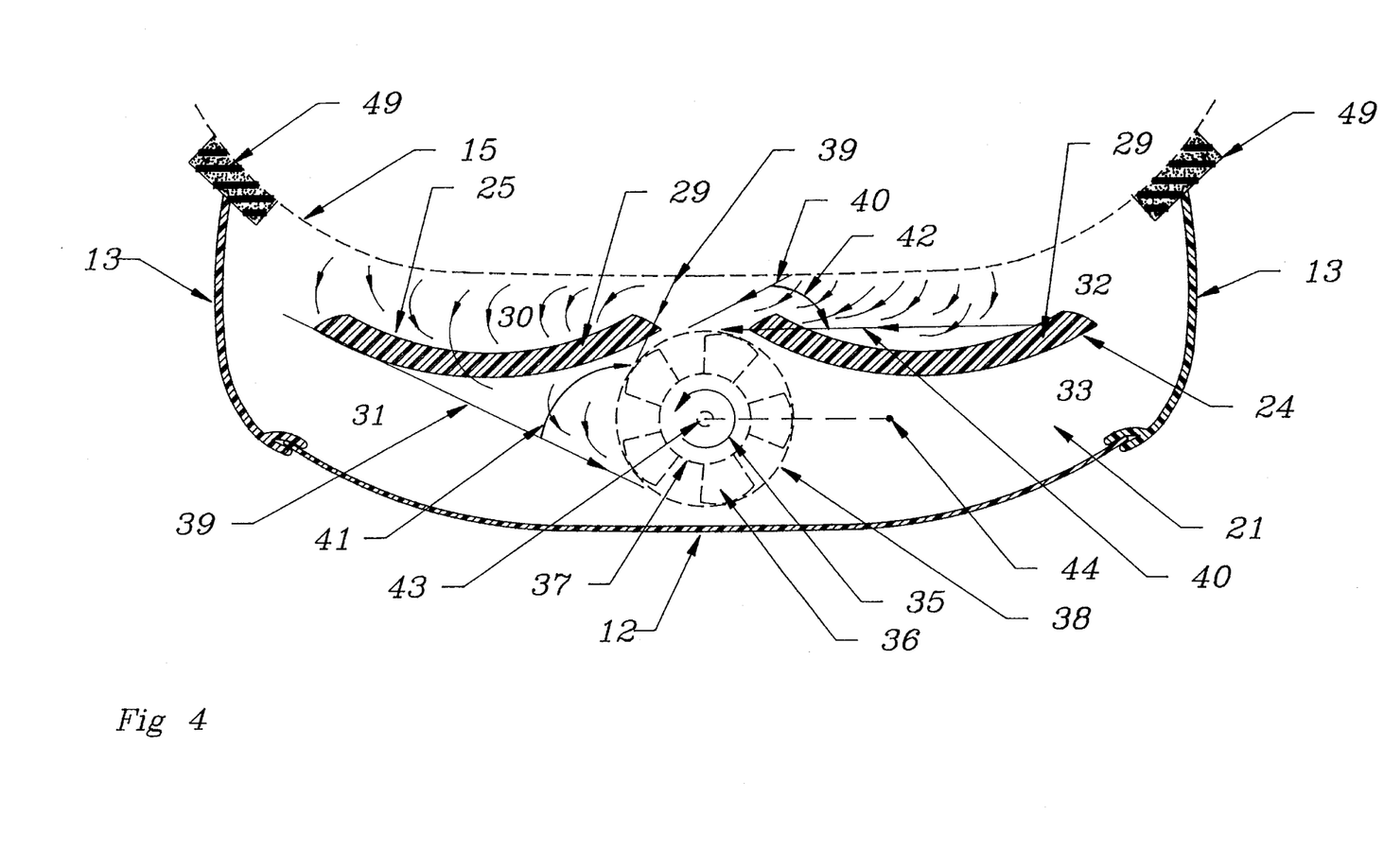
FIG. 4 is a horizontal cross-sectional view of the goggle of this invention, at the level of the top of a related eyeglass, taken generally in the plane of line 4—4 of FIG. 3.

It is commonly observed in operation of fan goggles 10 as illustrated in FIG. 1, that if fogging of related eyeglasses 23 occurs, only one of the lenses 24,25 fogs, but not the other. Thus, for an exhaust fan 11 which has a counterclockwise rotating fan shaft (when viewed from above and outside of goggle 10 as shown in FIG. 4), the left lens 24 will be observed to fog but not the right lens 25. Conversely, for an exhaust fan 11 which has a clockwise rotating shaft, the right lens 25 will be observed to fog, but not the left lens 24. If both lenses 24,25 are allowed to fog with the fan 11 not in operation, then the respective lens that tended to remain clear of fogging will clear substantially ahead of the opposite lens when the fan 11 is operated. This asymmetric defogging behavior is a major obstacle to achieving defogging by means of low capacity fan induced ventilation, and accordingly it is an advantage of the present invention that this asymmetric defogging behavior is prevented.

The cause of this asymmetric defogging behavior and means preventing such behavior can be understood by reference to FIG. 4. FIG. 4 is a top view of a horizontal cross section through the goggle 10 at the elevation of the top of the related eyeglasses 23, and shows the projection of the fan 11, including blade member 36, motor 37, and shroud 38 onto this cross-sectional plane. Air within the goggle air space 21 is drawn tangentially into the shroud 38. The angular extent over which such air intake occurs for the right inner goggle region 30 and the left inner goggle region 32 is shown by angular regions 41 and 42, respectively. The direction of rotation of blade member 36 is shown by rotation arrow 35. It is readily seen that the right inner goggle region 30 has superior angular access to the fan intake than the left inner goggle region 32. It can then be understood that right inner air flow 39 is superior to left inner air flow 40, and therefore, right lens 25 will show less fogging than left lens 24. Conversely, if the fan blade pitch of blade member 36 is reversed and rotation arrow 35 is reversed, the lenses 24,25 would be expected to show the reverse fogging tendencies, as is observed.

Figure 3:
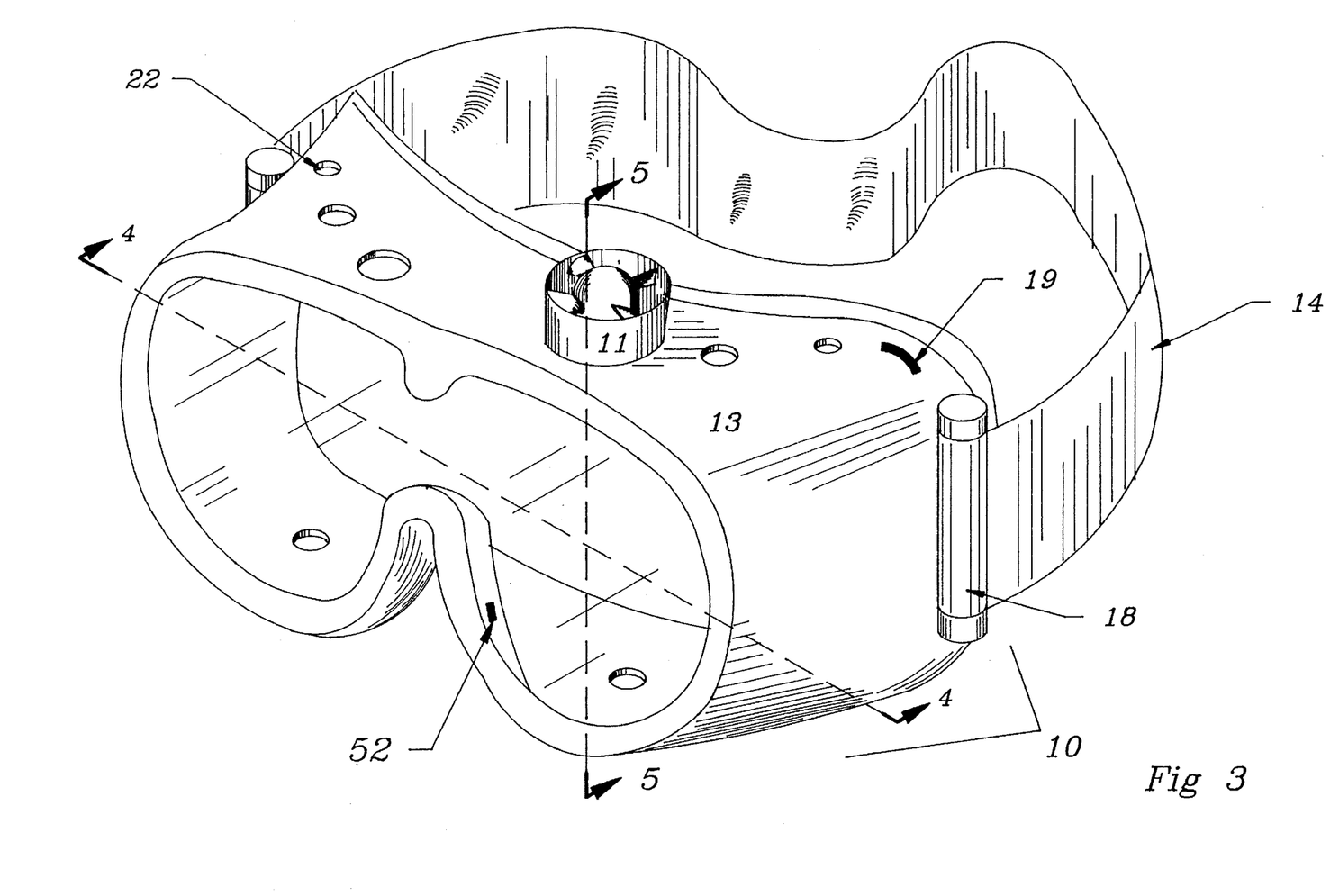
FIG. 3 is a perspective view of the goggle of this invention.

Nearly equal air flow for both inner goggle regions 30,32 can be achieved by shifting the fan 11 from a position with midplane fan axis 43 to a position with shifted fan axis 44, as shown in FIG. 4. With the axis of fan 11 positioned at shifted fan axis 44, the right angular region 41 decreases slightly, and the left angular region 42 increases substantially. Shifted fan axis 44 is chosen to give equal defogging of both right lens 25 and left lens 24. FIGS. 1 and 3 illustrate placement the fan on the top of the goggle frame, offset from the vertical plane which is centered between the right and left side of the goggle frame.

An alternative procedure which also improves defogging of one 24,25 relative to that of the other lens 24,25 is understood by reference to FIGS. 4 and 5. FIG. 5 is a vertical cross section of goggle 10 and face 16 in front of the eye 17, taken generally in the plane of line 5—5 of FIG. 3. In this alternate embodiment, the axis of fan 11 is tilted rearward by angle 45 within the goggle midplane. This procedure relies on the same principle as that described in the paragraph above, namely, the angular region 42 for air intake into the fan shroud 38 is significantly increased. This result is not specifically illustrated here, but could be seen by examining the appropriate angular region 41 and 42 in a plane perpendicular to fan axis 43 and passing across the top 29 of eyeglass 23, the position of said plane being indicated in FIG. 4 by line 50. The projection of fan shroud 38 on the plane containing line 50, would appear similar to FIG. 4, but would show that fan axis 43 has moved away from goggle region 32. This movement results in angular region 42 increasing in extent and thereby enhancing air flow 40.

Uniform inner air flow 39 and 40 can be beneficially maintained in part by insuring that the center of fan intake 46 is elevated above the top 29 of eyeglass 23. This distance is shown in FIG. 5 as intake elevation 48. An elevation 48 of 2 centimeters is effective in preventing fogging at fan capacity as low as 0.3 CFM, while an elevation 48 of zero centimeters has been observed to be ineffective at fan capacities as high as 1 CFM. This result can be understood, in that as the fan intake 46 approaches the top 29 of eyeglass 23, the air flow paths 39,40 are blocked. The use of air baffles and air ducts to divert air flow between goggle air space regions 30,31,32,33 has been found to be ineffective at low air flows utilized to minimize noise.

Figure 6:
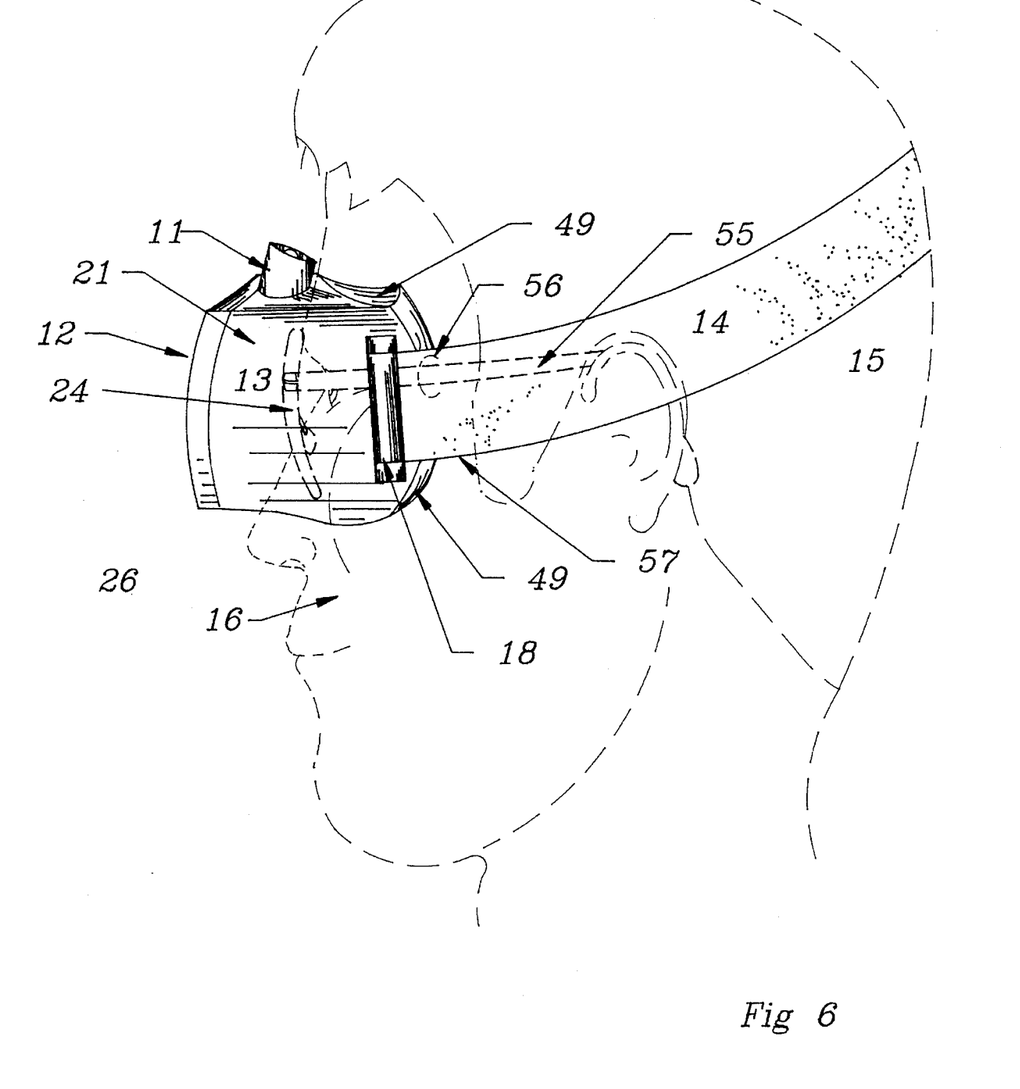
FIG. 6 is an end view of the side of the frame and temple port of an embodiment of this invention.

A further advantageous means to improve air flow at low rates when eyeglass 23 is worn in goggle air space 21 is the use of a ventilation port 56 in the general vicinity of the rear side of the goggle 11 as shown in FIG. 6. Eyeglass temple piece 55 generally passes through an opening 56 in goggle frame 13. In modern ski goggles, opening 56 is usually cushionably closed against the skier's head 15 by foam gasket 49 extending across opening 56. This foam gasket 49 is air permeable, but is overly restrictive of air passage at the low fan rates necessary to avoid unpleasant noise. The unrestricted opening 56 is particularly advantageous for the purposes of the present invention, as it allows outside air 26 to enter the goggle 10 at a point where eyeglass lenses 24,25 have maximum separation from face 16, and thereby allows unrestricted entry of outside air 26 into air spaces 30,31,32, 33. In addition outside air 26 is efficiently heated in the space 57 between the goggle strap 14 and skier's head 15, just before entering goggle air space 21, and continues to be convectively heated as it passes along face 16. It may be helpful to place an air baffle (not shown) along the bottom of strap 14 to discourage entry of exhaled breath 27 into air space 30,31,32,33.

Achievement of the goals of the present invention requires that fan 11 have particular characteristics with respect to both effective defogging and the generation of sound. As shown in FIG. 5, fan 11 consists of a blade member 36, an electric motor 37, and shroud 38 having a diameter allowing free rotation of blade member 36. Movement of blade member 36 through the air is a major source of noise. The intensity of sound emitted due to blade member 36 is a nonlinear function of the maximum velocity of blade member 36. This maximum velocity is given by the formula:

$$V_{max} = \pi \times (D_{max}/1000) \times (RPM/60),$$

where Vmax is the maximum velocity in meters per second of blade member 36, Dmax is the maximum diameter in millimeters of blade member 36, and RPM is the rotations per minute of blade member 36. The sound intensity due to rotation of blade member 36 is found to be approximately proportional to the sixth power of Vmax. Vmax values less than 7 meters per second produce sound levels which are not distracting, while Vmax values of less than 4 meters per second are inaudible.

Accordingly it can be understood that selecting a diameter and rotational rate for blade member 36 such that the value of Vmax is less than 7 meters per second is advantageous in achieving fan operation which is not distracting. However, reduction of either diameter or rotational rate of blade member 36 reduces the air capacity of fan 11, and may allow goggle 10 or related eyeglasses 23 to fog. Since fan air capacity is a linear function of the rotational rate of blade member 36 and a quadratic function of the diameter of blade member 36, it is overall more advantageous to reduce RPM than to reduce Dmax. Similarly, for a fixed sound level it is advantageous to increase Dmax and reduce RPM.

The amount by which Dmax can be increased is limited by the diameter of shroud 38 and goggle dimensions. Diameters up to 25 millimeters can be readily accommodated in an embodiment such as that shown in FIG. 1. Diameters up to 40 millimeters could be accommodated by mounting a fan on the side of frame 13, or on strap 14. Fans having 25 millimeter diameter shroud 38 can operate with Vmax values less than 7 meters per second and still provide air capacity in the optimum range between point (a) and point (b) of FIG. 2.

Small motors useful in the present invention show a significant level of mechanical vibration and it is therefore advisable to compliantly mount such a motor using gasket 28, such a form gasket, as shown in FIG. 5.

Figure 7:
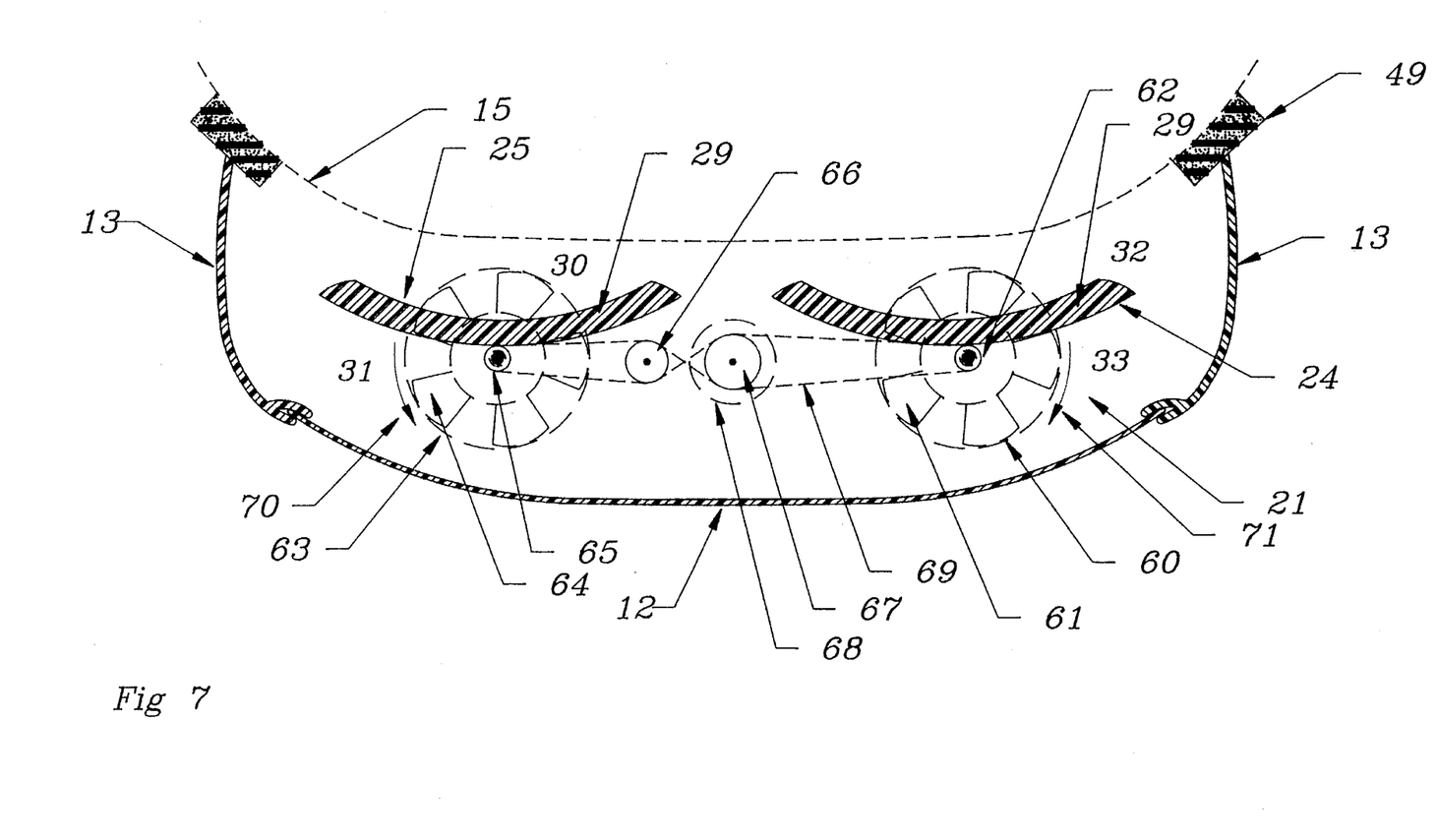
FIG. 7 is a horizontal cross-section view of the goggle of this invention, taken generally in the plane of line 4—4 of FIG. 3, showing an embodiment utilizing dual fans.

The use of two fans instead of one may be advantageous. Such an embodiment of the present invention is shown in FIG. 7. The fan mechanism are generally located in the top of goggle frame 13, which are shown in FIG. 7 superimposed on the same horizontal cross section as shown in FIG. 4. The two fan mechanisms of FIG. 7 consist of a right fan blade assembly 64 which rotates coaxially in the right shroud 63, and a left fan blade assembly 61 which rotates coaxially in the left shroud 60. Each blade assembly could have its own drive motor, but the embodiment of FIG. 7 advantageously uses a single drive motor 68. Each fan blade assembly 61 and 64 could operate at one-half the rotational speed of the single fan embodiment and produce the same volumetric capacity. This lower rotational speed would reduce the fan blade sound by roughly a factor of ⅕₄₅. Equal air flows in goggle space region 30 and 32 can be obtained if fan blade assemblies 61 and 64 counter rotate. This counter rotation, shown as right fan blade rotation direction 70 and left fan blade rotation direction 71 is achieved with the single drive motor 68 by means of a single drive belt 69 and a right blade pulley 65, a left blade pulley 62, a drive motor pulley 67, and a set of belt crossover pulleys 66. A power source for the two fan embodiment can consist of a small electrical battery housed in a battery compartment 18, and an on/off switch 19 as shown in FIG. 1.

The electric motor 37 can be connected directly to the power source (not shown) through a switch means 19 for turning power on or off. The power source is most conveniently one or more electric batteries and are shown in FIG. 3 as being housed in a compartment 18 in frame 13. It may be beneficial to use a motor speed controller 20 to set the capacity of fan 11 within the optimum range of FIG. 2, between point (a) and point (b). It may also be advantageous to utilize a motor speed controller 20 which is capable of fan speed operation at several different speeds, so that fan operation can be adjusted for various weather conditions.

Modern ski goggles frequently use an open ventilation design which can be understood with reference to FIG. 3. In such an open design, the frame ports 22 occupy nearly all of the area of the top and bottom of the goggle frame 13. Ports 22 are generally covered with thin air permeable foam, which allows outside air 26 to enter the goggle air space 21, but prevents snow from entering space 21. When the skier is in rapid motion, outside air 26 readily enters the goggle air space 21 causing the temperatures of lens 12 and lenses 24,25 to drop, causing wind chill effects on face 16, and allowing exhaled breath 27 to enter goggle air space 21. This reduces comfort of the skier and may cause lens 12 and lenses 24,25 to fog. The forced ventilation techniques disclosed in the present invention allow frame ports 22 along the top of frame 13 to be eliminated. The only exhaust port then is shroud 38. All ports 22 on the bottom of frame 13 can also be eliminated, thereby significantly reducing the likelihood of exhaled breath 27 entering goggle air space 21. Elimination of ports 22 results in generally higher temperature of goggle air space 21, and therefore less fogging of lens 12 and lenses 24,25, as well as maintenance of higher goggle air space temperature even when the skier is in rapid motion.

An operative examples of an embodiment of the present invention which includes the features described herein has been evaluated for defogging, sound level, and skier comfort. This operative embodiment has a fan mounted in the top center of the goggle frame as illustrated in FIG. 1, tipped rearward as illustrated in FIG. 5. The fan motor 37 of this fan 11 is an electronic commutation type and has a volumetric capacity of 1.3 CFM at 13,000 RPM with a shroud diameter of 25 mm. The fan air intake is positioned 2 centimeters above the top of the eye socket. The goggle frame is generally closed and the air intake is as shown in FIG. 6 and is unobstructed by foam material. Using the Fogging Test described in Section 2.1, the goggle defogs in 20 seconds and prevents fog formation when operated at 0.6 CFM; and defogs in 45 seconds and prevents fog formation when operated at 0.3 CFM. The fan of this goggle is inaudible when the skier is in motion or on a chair lift, for example. The sound emission level is estimated at zero decibels at a distance of one meter. When the skier is in motion, no noticeable wind chill effects on the eyes are observed. An embodiment with an offset fan gave similar performance to the tipped fan.

The invention has been described in detail with particular references to preferred embodiments thereof. As will be apparent to those skilled in the art in the light of the accompanying disclosure, many alterations, substitutions, modifications, and variations are possible in the practice of the invention without departing from the spirit of the invention.

I claim:

1. A goggle with defogging means to be worn on the face of a user, comprising:
   - (a.) a frame member suitable for placing in contact with the face of the user, said frame member having a top, a bottom, a left side, and a right side, and a lens member supported by said frame member, said frame member securing said lens member in a position so that the user looks through the lens member when the frame member is placed in contact with the face, wherein a center line bisecting the top of said frame member is an equal distance from the left side and the right side of the frame member,
   - (b.) strap means to removably maintain said frame member in said position,
   - (c.) air exhaust means supported by said frame member for exhausting air from an air space between said frame member, said lens member, and the face of the user to ambient air exterior to the goggle, said air exhaust means comprising a fan blade assembly located within a fan blade shroud, which fan blade assembly is connected to an electric motor so that said fan blade assembly rotates coaxially within said blade shroud when said electric motor is activated, and
   - (d.) power supply means for supplying power to said electric motor, and
   - (e.) wherein said air exhaust means is mounted on the top of said frame member an offset distance from said center line.

2. The goggle as described in claim 1, wherein said frame member secures said lens a sufficient distance from the face of the user to permit the user to wear in said air space eyeglasses comprising eyeglass lenses and a frame with a right temple piece and a left temple piece.

3. The goggle as described in claim 1, wherein the air exhaust means causes air to be exchanged between said air space and air exterior to the goggle at an exchange rate which maintains a measurable dew point of said air space at a temperature less than a measurable temperature of the lens member.

4. A goggle with defogging means to be worn on the face of a user, comprising:
   - (a.) a frame member suitable for placing in contact with the face of the user, said frame member having a top, a bottom, a left side, and a right side, and a lens member supported by said frame member, said frame member securing said lens member in a position so that the user looks through the lens member when the frame member is placed in contact with the face,
   - (b.) strap means to removably maintain said frame member in said position,
   - (c.) air exhaust means supported by said frame member for exhausting air from an air space between said frame member, said lens member, and the face of the user to ambient air exterior to the goggle, said air exhaust means comprising a fan blade assembly located within a fan blade shroud, which fan blade assembly is connected to an electric motor so that said fan blade assembly rotates coaxially within said blade shroud when said electric motor is activated, and
   - (d.) power supply means for supplying power to said electric motor,
   - (e.) wherein said bottom of said frame member is substantially impermeable to air so that ambient air external to the goggle cannot flow through said bottom of said frame member into said air space, and
   - (f.) wherein said frame member secures said lens a sufficient distance from the face of the user to permit the user to wear in said air space eyeglasses comprising eyeglass lenses and a frame with a right temple piece and a left temple piece, and
   - (g.) ventilation ports formed in said right side and said left side of said frame member, which ventilation ports are suitable for permitting eyeglass temple pieces to extend from inside said air space to the user's ears exterior to the goggle wherein said air external to the goggle is permitted to flow into said air space during operation of said electric motor only through said ventilation ports.

5. The goggle as described in claim 4, wherein the air exhaust means causes air to be exchanged between said air space and air exterior to the goggle at an exchange rate which maintains a measurable dew point of said air space at a temperature less than a measurable temperature of the eyeglass lenses.

6. The goggle as described in claim 1, wherein said air exhaust means is immovably mounted on the top of said frame member between said center line and said right side of the frame and wherein said fan blade assembly of said air exhaust means rotates in a clockwise direction when viewed from above said goggle.

7. The goggle as described in claim 1, wherein said air exhaust means is immovably mounted on the top of said frame member between said center line and said left side of the frame and wherein said fan blade assembly of said air exhaust means rotates in a counter-clockwise direction when viewed from above said goggle.

8. A goggle with defogging means to be worn on the face of a user, comprising:
   - (a.) a frame member suitable for placing in contact with the face of the user, said frame member having a top, a bottom, a left side, and a right side, and a lens member supported by said frame member, said frame member securing said lens member in a position so that the user looks through the lens member when the frame member is placed in contact with the face,
   - (b.) strap means to removably maintain said frame member in said position,
   - (c.) air exhaust means supported by said frame member for exhausting air from an air space between said frame member, said lens member, and the face of the user to ambient air exterior to the goggle, said air exhaust means comprising a fan blade assembly located within a fan blade shroud, which fan blade assembly is connected to an electric motor so that said fan blade assembly rotates coaxially within said blade shroud when said electric motor is activated, and
   - (d.) power supply means for supplying power to said electric motor,
   - (e.) wherein said air exhaust means is mounted on the top of said frame member and a vertical axis of said fan blade assembly forms an acute angle with a horizontal plane in which the top of said frame member lies.

9. A goggle with defogging means to be worn on the face of a user, comprising:
- (a.) a frame member suitable for placing in contact with the face of the user, said frame member having a top, a bottom, a left side, and a right side, and a lens member supported by said frame member, said frame member securing said lens member in a position so that the user looks through the lens member when the frame member is placed in contact with the face,
- (b.) strap means to removably maintain said frame member in said position,
- (c.) air exhaust means supported by said frame member for exhausting air from an air space between said frame member, said lens member, and the face of the user to ambient air exterior to the goggle, said air exhaust means comprising a fan blade assembly located within a fan blade shroud, which fan blade assembly is connected to an electric motor so that said fan blade assembly rotates coaxially within said blade shroud when said electric motor is activated, and
- (d.) power supply means for supplying power to said electric motor,
- (e.) wherein said fan blade assembly has a maximum linear velocity of less than seven meters per second while said electric motor is activated.

10. A goggle with defogging means to be worn on the face of a user, comprising:
- (a.) a frame member suitable for placing in contact with the face of the user, said frame member having a top, a bottom, a left side, and a right side, and a lens member supported by said frame member, said frame member securing said lens member in a position so that the user looks through the lens member when the frame member is placed in contact with the face,
- (b.) strap means to removably maintain said frame member in said position,
- (c.) air exhaust means supported by said frame member for exhausting air from the air space between said frame member, said lens member, and the face of the user to ambient air exterior to the goggle, said air exhaust means comprising two exhaust fan blade assemblies, each fan blade assembly located within a fan blade shroud, which fan blade assemblies are connected to at least one electric motor so that each fan blade assembly rotates coaxially within the blade shroud and in an opposite direction of rotation with respect to the other fan blade assembly when each electric motor is activated, and
- (d.) power supply means for supplying power to each electric motor.

11. The goggle as described in claim 9, wherein air enters said fan blade shroud of said air exhaust means at a vertical elevation of no less than 3 centimeters above pupils of the user's eyes when the goggle is in said position on the user's face.

* * * * *